US012735665B2

(12) United States Patent
Yotsuya et al.

(10) Patent No.: US 12,735,665 B2
(45) Date of Patent: Sep. 15, 2026

(54) GAS-PERMEABLE CONTAINER, AND CULTURE APPARATUS AND CULTURE SYSTEM EACH USING SAME

(71) Applicant: JUNKOSHA INC., Ibaraki (JP)

(72) Inventors: Masato Yotsuya, Ibaraki (JP); Mitsuru Kuroda, Ibaraki (JP)

(73) Assignee: JUNKOSHA INC., Ibaraki (JP)

( * ) Notice: Subject to any disclaimer, the term of this patent is extended or adjusted under 35 U.S.C. 154(b) by 642 days.

(21) Appl. No.: 18/034,813

(22) PCT Filed: Oct. 29, 2021

(86) PCT No.: PCT/JP2021/040100
§ 371 (c)(1),
(2) Date: May 1, 2023

(87) PCT Pub. No.: WO2022/097582
PCT Pub. Date: May 12, 2022

(65) Prior Publication Data

US 2024/0002765 A1 Jan. 4, 2024

(30) Foreign Application Priority Data

Nov. 5, 2020 (JP) ................................ 2020-185456
Nov. 17, 2020 (JP) ................................ 2020-191254
(Continued)

(51) Int. Cl.
*C12M 1/04* (2006.01)
*C12M 1/34* (2006.01)

(52) U.S. Cl.
CPC ........... *C12M 23/24* (2013.01); *C12M 41/12* (2013.01)

(58) Field of Classification Search
None
See application file for complete search history.

(56) References Cited

U.S. PATENT DOCUMENTS

2008/0299649 A1* 12/2008 Martin .................. C12M 23/38 435/297.1
2010/0055790 A1* 3/2010 Simon ................... C12M 23/12 435/297.1
(Continued)

FOREIGN PATENT DOCUMENTS

CN 105051175 B 11/2016
CN 105992816 B 4/2018
(Continued)

OTHER PUBLICATIONS

Zhang et al., A Disposable Microfluidic Virus Concentration Device Based on Evaporation and Interfacial Tension, Diagnostics 2013, 3, 155-169 (Year: 2013).*
(Continued)

*Primary Examiner* — Holly Kipouros
(74) *Attorney, Agent, or Firm* — Paratus Law Group, PLLC

(57) ABSTRACT

The present invention relates to a gas-permeable container, and for example, to a gas-permeable container suitable for culturing aerobic microorganisms or animal or plant cells. An object of the present invention is to provide a container having excellent gas permeability, and a culture apparatus and a culture system each using the container. The object is achieved by a gas-permeable container according to the present invention to be used while storing a liquid, in which at least the container uses a membrane material having a ratio of water evaporation amounts of about 1.1 or more.

6 Claims, 6 Drawing Sheets

(30) Foreign Application Priority Data

| | | |
|---|---|---|
| Feb. 18, 2021 | (JP) | 2021-024723 |
| Mar. 1, 2021 | (JP) | 2021-032137 |

(56) References Cited

U.S. PATENT DOCUMENTS

| | | | | |
|---|---|---|---|---|
| 2013/0295660 | A1 | 11/2013 | Fey | |
| 2018/0320122 | A1 | 11/2018 | Blanchard | |
| 2019/0127674 | A1* | 5/2019 | Lacey | B01L 3/08 |
| 2020/0172695 | A1* | 6/2020 | Park | B01D 67/0027 |
| 2022/0186165 | A1 | 6/2022 | Johnson et al. | |

FOREIGN PATENT DOCUMENTS

| | | | | | |
|---|---|---|---|---|---|
| EP | 2963106 | A1 | | 1/2016 | |
| JP | H11-187868 | A | | 7/1999 | |
| JP | 2001-190267 | A | | 7/2001 | |
| JP | 2003-079360 | A | | 3/2003 | |
| JP | 2010075081 | A | * | 4/2010 | C12M 33/00 |
| JP | 2011-083263 | A | | 4/2011 | |
| JP | 2012-239401 | A | | 12/2012 | |
| JP | 2018-015751 | A | | 2/2018 | |
| JP | 2018-019615 | A | | 2/2018 | |
| JP | 2019-107036 | A | | 7/2019 | |
| TW | 201529843 | A | | 8/2015 | |
| TW | 201614062 | A | | 4/2016 | |
| WO | WO-2009039433 | A1 | * | 3/2009 | C12M 23/16 |
| WO | WO 2015/073913 | A1 | | 5/2015 | |
| WO | WO 2015/102529 | A1 | | 7/2015 | |
| WO | WO 2015/188106 | A2 | | 12/2015 | |
| WO | WO 2016/106280 | A1 | | 6/2016 | |
| WO | WO 2020/219834 | A1 | | 10/2020 | |

OTHER PUBLICATIONS

Document titled JP2010075081A Tool for Conveying Cell Sheet, machine translation of JP 2010075081 A provided by Espacenet, original document published 2010 (Year: 2010).*

May 14, 2025, Taiwanese Office Action issued for related TW Application No. 110140795.

Aug. 28, 2025, Japanese Office Action issued for related JP Application No. 2022-560756.

Jan. 11, 2022, Translation of International Search Opinion issued for related PCT Application No. PCT/JP2021/040100.

May 8, 2026, European Search Report issued for related EP Application No. 21889135.6.

* cited by examiner

GAS-PERMEABLE CONTAINER, AND CULTURE APPARATUS AND CULTURE SYSTEM EACH USING SAME

CROSS REFERENCE TO PRIOR APPLICATION

This application is a National Stage Patent Application of PCT International Patent Application No. PCT/JP2021/040100 (filed on Oct. 29, 2021) under 35 U.S.C. § 371, which claims priority to Japanese Patent Application Nos. 2020-185456 (filed on Nov. 5, 2020), 2020-191254 (filed on Nov. 17, 2020), 2021-024723 (filed on Feb. 18, 2021), and 2021-032137 (filed on Mar. 1, 2021), which are all hereby incorporated by reference in their entirety.

TECHNICAL FIELD

The present invention relates to a gas-permeable container. For example, the present invention relates to a container suitable for culturing aerobic microorganisms or animal or plant cells, and also relates to a culture apparatus and a culture system using the container.

BACKGROUND ART

Culturing of microorganisms or cells using a liquid culture medium has been performed in small amounts in a laboratory using a small container such as a Petri dish and a culture flask at a research stage. However, in recent years, with development of biopharmaceuticals that produce antibodies and functional proteins by using CHO cells, regenerative medicine that uses iPS cells and the like, immunotherapy, and the like, there is a demand for culturing a large amount of cells or microorganisms in a short period of time. As a method for culturing a large amount of cells or microorganisms, a shaking method (Patent Literature 1) has been proposed in which air and a culture medium are sealed together in a bag-shaped culture bag, and the culture medium is agitated by shaking for culturing, and a method has been proposed in which a culture medium and microorganisms or cells are placed in a large container such as a stainless steel tank (Patent Literature 2).

It is known that aerobic microorganisms or animal or plant cells consume more oxygen when density of the aerobic microorganisms or animal or plant cells in a culture medium increases, resulting in a decrease in a dissolved oxygen concentration of the culture medium and a slow growth rate. In order to culture a large amount of aerobic microorganisms or animal or plant cells at one time, it is necessary to dissolve sufficient oxygen in a culture medium to supply oxygen to the microorganisms or cells. Therefore, a method using a culture container such as a gas-permeable culture bag (Patent Literature 3), a method of supplying oxygen by dispersing an oxygen-supplied hydrophobic solvent into a culture medium in a culture tank by using an oxygen absorbing device using a highly oxygen-permeable membrane, and transferring oxygen from the hydrophobic solvent to the culture medium (Patent Literature 4), and the like are studied.

However, it was difficult to supply sufficient oxygen to an entire culture medium by the conventional methods, and these methods cannot obtain a sufficient dissolved oxygen concentration to efficiently culture aerobic microorganisms or animal or plant cells at high density.

PRIOR ART DOCUMENTS

Patent Literatures

Patent Literature 1: JP2019-107036A
Patent Literature 2: JP2011-83263A
Patent Literature 3: JP2012-239401A
Patent Literature 4: JP1999-187868A

SUMMARY OF INVENTION

Object to be Achieved by the Invention

In view of the conventional problem as described above, an object of the present invention is to provide a container having excellent gas permeability, and to provide a culture apparatus and a culture system each using the container.

Means for Achieving Object

As a result of examination in view of the above-described object, the present invention has been completed. Specifically, the above-mentioned object can be achieved by a gas-permeable container to be used while storing a liquid, in which at least the container uses a membrane material having a ratio of water evaporation amounts of about 1.1 or more. Further, the gas-permeable container preferably has a water evaporation amount per unit liquid contact area of the gas-permeable container of about 0.01 kg/($m^2$·h) to about 1.0 kg/($m^2$·h).

Further, in the gas-permeable container according to the present invention, the membrane material is preferably formed by using at least one selected from polyolefin and fluororesin, and the membrane material may be formed by using at least polytetrafluoroethylene.

Further, the present invention relates to a culture system in which the gas-permeable container is used. In addition, the culture system preferably further includes a sensor configured to detect an amount of the liquid in the gas-permeable container, and a liquid supply device configured to supply the liquid into the gas-permeable container. Further, the culture system may further include a temperature adjusting device that adjusts a temperature of the liquid in the gas-permeable container. Further, the present invention relates to a culture method for performing culture while adjusting an amount of the liquid in the gas-permeable container by using the culture system.

In addition, the above-mentioned object can be achieved by a culture apparatus including: a gas-permeable container; an outer wall covering at least a part of the gas-permeable container; and a gas communication unit configured to send gas between the gas-permeable container and the outer wall, in which the gas-permeable container is a container to be used while storing a liquid, and at least the container uses a membrane material having a ratio of water evaporation amounts of about 1.1 or more. Further, the gas-permeable container preferably has a water evaporation amount per unit liquid contact area of the gas-permeable container of about 0.01 kg/($m^2$·h) to about 1.0 kg/($m^2$·h).

In the gas-permeable container provided in the culture apparatus according to the present invention, the membrane material is preferably formed by using at least one selected from polyolefin and fluororesin, and the membrane material may be formed by using at least polytetrafluoroethylene.

The present invention relates to a culture system in which the culture apparatus is used. The culture system preferably further includes a sensor configured to detect an amount of the liquid in the gas-permeable container provided in the culture apparatus, and a liquid supply device configured to supply the liquid into the gas-permeable container. Further, the culture system may further include a temperature adjusting device that adjusts a temperature of the liquid in the gas-permeable container. Further, the present invention relates to a culture method for performing culture while adjusting an amount of the liquid in the gas-permeable container by using the culture system.

Effects of Invention

A gas-permeable container according to the present invention can have unprecedentedly excellent gas permeability. Further, a culture apparatus and a culture system each using the gas-permeable container according to the present invention enable aerobic microorganisms or animal or plant cells to be cultured at high density in a culture medium.

EMBODIMENT FOR CARRYING OUT THE INVENTION

Embodiments of a gas-permeable container and a culture apparatus and a culture system each using the container according to the present invention will be described in detail below.

Figure 1:
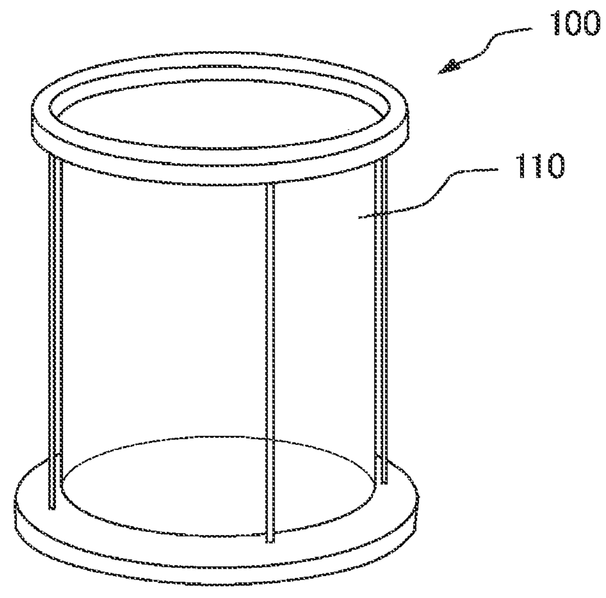
FIG. 1 is a diagram showing an example of using a gas-permeable container according to the present invention.

FIG. 1 is a diagram showing an example of using a gas-permeable container according to the present invention. An apparatus 100 in FIG. 1 is an example of a vertical apparatus including a gas-permeable container 110, a bottom support plate, and pillars. The gas-permeable container according to the present invention can be applied, for example, from a development model size with a capacity of about 100 mL to a plant size with a capacity of about 2000 L for mass cultivation. The vertical aspect is present as shown in FIG. 1, and a horizontal aspect such as a dish shape or an envelope shape is also possible. From a viewpoint of preventing liquid leakage due to an internal pressure during use, the gas-permeable container according to the present invention preferably has a water pressure resistance of 300 kPa or more, more preferably 350 kPa or more.

The gas-permeable container according to the present invention can increase a dissolved oxygen concentration of a liquid in the gas-permeable container, and is suitable as an example for culturing aerobic microorganisms, animal or plant cells, and the like. For the gas-permeable container according to the present invention, it is preferable to use a membrane material having a ratio of water evaporation amounts of about 1.1 or more. The ratio of water evaporation amounts of the membrane material is more preferably from about 1.1 to about 5.0, further preferably from about 1.1 to about 4.0, and still more preferably from about 1.1 to about 3.5. The ratio of water evaporation amounts can be considered as a standard of ease of oxygen transfer from outside of the gas-permeable container to the liquid inside the gas-permeable container, and the gas-permeable container in which the membrane material with a high ratio of water evaporation amounts is used for at least a part of a liquid-contacting portion can maintain a high dissolved oxygen concentration of the liquid.

A volumetric oxygen transfer coefficient $k_La$ is often used as an index of an oxygen supply capacity of a culture container. $k_La$ is a parameter representing a speed at which oxygen in a gas phase moves to a liquid phase, and can be obtained by experiments. The volumetric oxygen transfer coefficient $k_La$ is a value obtained by multiplying a liquid-side mass transfer coefficient $k_L$ $[m \cdot h^{-1}]$ by the gas-liquid contact area a $[m^{-1}]$ per unit volume. Here, a correlation between the liquid-side mass transfer coefficient $k_L$ and the water evaporation amount is confirmed for the membrane material used for the gas-permeable container according to the present invention. Regarding the membrane material used for the gas-permeable container according to the present invention, a liquid-side mass transfer coefficient $k_L$ ($k_L$ (DRY)) when the membrane material is not in contact with water, a liquid-side mass transfer coefficient $k_L$ ($k_L$ (WET)) when the membrane material is in contact with water, a water evaporation amount (WE (DRY)) when the membrane material is not in contact with water, and a water evaporation amount (WE (WET)) when the membrane material is in contact with water are measured. The measured results are shown below.

$k_L$ (DRY): 0.065 m/h, $k_L$ (WET): 0.142 m/h, $k_L$ (WET)/$k_L$ (DRY): 2.2

WE (DRY): 0.21 kg/($m^2 \cdot h$), WE (WET): 0.44 kg/($m^2 \cdot h$), WE (WET)/WE (DRY): 2.1

From the above-mentioned results, $k_L$ (WET)/$k_L$ (DRY) and WE (WET)/WE (DRY) show almost the same value, and it can be seen that the water evaporation amount has a certain degree of the correlation with the liquid-side mass transfer coefficient $k_L$. Hereinafter, WE (WET)/WE (DRY) will be referred to as the "ratio of water evaporation amounts".

In the gas-permeable container according to the present invention, the volumetric oxygen transfer coefficient $k_La$ can be increased by using a membrane material having a higher ratio of water evaporation amounts. For example, when measuring a volumetric oxygen transfer coefficient $k_La$ of a glass culture container conventionally used, $k_L$ a is approximately 0.72/h, whereas in one example of the gas-permeable container according to the present invention, $k_La$ can be approximately 2.0/h or more.

From experimental results regarding the water evaporation amount and the liquid-side mass transfer coefficient $k_L$ described above, it is considered that the ratio of water evaporation amounts is related to a size of an area of a gas-liquid interface formed through the membrane material when viewed microscopically. The size of the area of the gas-liquid interface can be adjusted, for example, by a structure of a surface of the membrane material (for example, an average length RSm of profile elements on the surface).

As a membrane material having an adjusted surface structure, for example, a membrane material having a porous structure (hereinafter, referred to as membrane material with porous structure) can be used. As the membrane material with porous structure, a sheet of polytetrafluoroethylene (PTFE) or high-density polyethylene which is made porous by expanding can be used. When a sheet with porous structure is used as the membrane material of the gas-permeable container, a sheet with porous structure and a sheet with solid structure can be laminated to form the membrane material. When the laminated sheets are used as the membrane material, it is preferable to dispose the sheet with porous structure on a liquid-contacting side surface, and it is more preferable that a thickness of the sheet with porous structure accounts for 5% or more of a thickness of the membrane material. When only the sheet with porous structure constitutes the membrane material of the gas-permeable container, it is more preferable to use a hydrophobic material from a viewpoint of preventing liquid leakage from the gas-permeable container. It is also possible to use a sheet with porous structure which is imparted with hydrophobicity by, for example, surface treatment. When only the sheet with porous structure constitutes the membrane material of the gas-permeable container, the water pressure resistance of the gas-permeable container or the membrane material of the gas-permeable container is preferably 300 kPa or more, and more preferably 350 kPa or more. It is more preferable that a bubble point change rate between a bubble point of the membrane material of the gas-permeable container before conducting a water pressure resistance test and a bubble point of the membrane material of the gas-permeable container after conducting the water pressure resistance test is within about 15%. In the water pressure resistance test, a water pressure is applied to a wall of the gas-permeable container or the membrane material constituting the gas-permeable container, and the pressure is applied until water leaks out and the pressure is measured. When only the sheet with porous structure constitutes the membrane material of the gas-permeable container, the membrane material includes a thin membrane formed with pores and easily deformed parts such as fine fibers inside, and the porous structure is easily deformed by high pressure, but the matter that the bubble point change rate is kept within about 15% indicates that the deformation of the porous structure of the membrane material is kept small.

Examples of another membrane material having an adjusted surface structure include a sheet produced by electrospinning, a sheet in which micropores are formed by laser processing, and a non-woven fabric. Various resins can be used for these materials.

The gas-permeable container according to the present invention preferably has a water evaporation amount per unit liquid contact area of the container of about 0.01 kg/(m$^2$·h) to about 1.0 kg/(m$^2$·h). The water evaporation amount per unit liquid contact area of the container is more preferably from about 0.05 kg/(m$^2$·h) to about 0.8 kg/(m$^2$·h), further preferably from about 0.05 kg/(m$^2$·h) to about 0.5 kg/(m$^2$·h), and most preferably from about 0.1 kg/(m$^2$·h) to about 0.5 kg/(m$^2$·h). When the liquid reduced due to evaporation is supplied from the outside of the system, sufficient oxygen is dissolved in the supplied liquid, which is suitable for culture performance. However, even if the water evaporation amount becomes too large, it is not preferable because the evaporation of water causes adverse effects.

The gas-permeable container according to the present invention preferably uses a membrane material formed by using at least one selected from polyolefin and fluororesin. Examples of polyolefin include low-density polyethylene (LDPE), linear low-density polyethylene (LLDPE), and polypropylene. Further, polyurethane (PUR), polystyrene (PS), polyimide (PI), and the like can also be used. Further, the gas-permeable container according to the present invention is preferably formed by using a thermoplastic resin.

Further, the gas-permeable container according to the present invention may be formed by using a membrane material for which at least polytetrafluoroethylene (PTFE) is used. PTFE used for the membrane material may be a homopolymer of tetrafluoroethylene (hereinafter, referred to as "TFE") or modified PTFE containing a small amount of monomers other than TFE.

The resin used for the membrane material of the gas-permeable container according to the present invention may contain a filler or other resins, if necessary. Examples of the filler include carbon, metal oxides of alumina and the like, and a resin filler, and examples of other resins include thermoplastic fluororesin, polystyrene, thermoplastic polyimide, and thermosetting resin. These examples can be used alone or in combination.

A method for producing the gas-permeable container according to the present invention will be described below by taking a case, as an example, of using a sheet with porous structure of PTFE for the membrane material constituting the gas-permeable container according to the present invention.

The sheet with porous structure of PTFE used for the membrane material of the gas-permeable container according to the present invention can be produced by mixing PTFE fine powder and an auxiliary agent, molding the mixture into a sheet shape, and then expanding the sheet-shaped PTFE. For example, the sheet with porous structure can be made as one having a density of 0.25 g/cm$^3$ to 1.5 g/cm$^3$.

The membrane material of the gas-permeable container according to the present invention may be a laminate of a plurality of sheets including the sheet with porous structure of PTFE, and may include a sheet with porous structure of a different resin, a sheet with solid structure, or the like, in addition to the sheet with porous structure of PTFE. In that case, the sheet portion with porous structure preferably accounts for 5% or more, and more preferably 10% or more in the thickness of the membrane material. The thickness of the membrane material of the gas-permeable container can be set such that the water pressure resistance and a strength of the container and the water evaporation amount are within suitable ranges. For example, the thickness of the membrane material of the gas-permeable container is preferably 0.01 mm to 3.0 mm, and more preferably 0.03 mm to 2.0 mm.

The gas-permeable container can be formed, for example, in the following manner, for example, in a case of using a laminate of a plurality of sheets as the membrane material of the gas-permeable container. The sheet is wound around a cylindrical mandrel to form a laminate which forms a side of the container, and a circular sheet which forms a bottom of the container is attached to one end of the laminate, and a beaker-shaped laminate is obtained. The container can be obtained by further attaching a lid to this beaker-shaped laminate. By forming in this way, it is possible to obtain an inner surface of the container without steps such as seams and grooves. The cylindrical mandrel to be used is preferably selected according to a size of the container to be produced, and when the container is produced by this method, it is preferable to use a mandrel with a diameter of, for example, about 50 mm to 1000 mm due to easy handling, an example is an aluminum mandrel with a diameter of 100 mm and a length of 500 mm, and in this case, a container with a capacity of about 3.5 L can be produced. As an example of using the sheet with porous structure of PTFE as the membrane material of the gas-permeable container, the sheet with porous structure of PTFE is wound on the mandrel a required number of times to produce a cylindrical PTFE laminate, a circular sheet which forms the bottom of the container is attached to one end to form a beaker-shaped laminate, and the laminate is sintered by heating at a temperature of 360° C. or higher for 40 minutes or longer while covering the mandrel. After cooling the sintered PTFE laminate and removing the PTFE laminate from the mandrel so that the beaker shape is maintained, the lid is attached and the container is obtained.

Further, for the membrane material of the gas-permeable container, the sheet with porous structure, the sheet with solid structure (solid sheet), and different materials such as different resins can be used in combination. In that case, for example, when the sheets are wound around the mandrel, the various sheets may be disposed and laminated at required positions. Further, the laminate formed by laminating the sheets into a cylindrical shape is used, and a part thereof is cut and attached with another sheet to form a container, or it is also possible to form a cylindrical laminate by winding various sheets around a mandrel, then cut open to form sheets, and combine the sheets to form a container.

Figure 2:
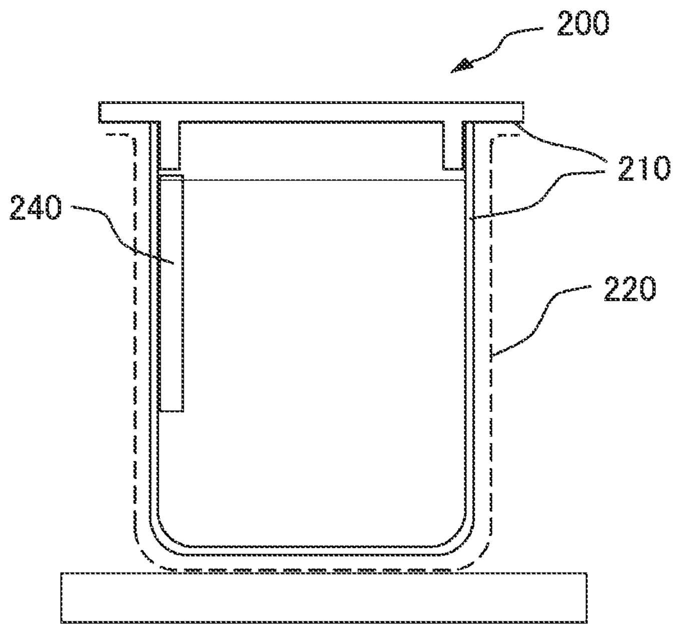
FIG. 2 shows an example of a culture system using the gas-permeable container according to the present invention.

FIG. 2 is a diagram illustrating an example of a culture system using the gas-permeable container according to the present invention. The example of FIG. 2 is one of examples of the culture system with simplest configuration in the culture system according to the present invention. The gas-permeable container according to the present invention can supply sufficient oxygen when used for culturing microorganisms or cells, can also discharge unnecessary gaseous waste products such as carbon dioxide generated during culture, and culture can be performed in a system with simple structure. For example, in FIG. 2, a culture system 200 includes a gas-permeable container 210, a holder 220 that holds the gas-permeable container 210, and a liquid supply device 240 that detects an amount of a liquid in the gas-permeable container 210 and supplies the liquid into the container. The holder 220 that holds the gas-permeable container 210 preferably has a structure that does not hinder evaporation of water, that is, permeation of gas, and preferably has, for example, a mesh structure made of metal, hard plastic, or the like, and has a strength capable of limiting deformation of the gas-permeable container 210 due to a weight of the liquid in the container or the like. Here, the gas-permeable container according to the present invention can be used while storing a liquid, and when the gas-permeable container is filled with a liquid, the inner surface is in contact with the liquid, and an outer surface opposite thereto is in contact with gas, and the gas-permeable container is a smallest functional unit that can be sealed to prevent liquid leakage. In the example of FIG. 2, the gas-permeable container 210 stores the liquid inside during use, and a surface, on an inner side of the container, of the membrane material constituting the gas-permeable container 210 is in contact with the liquid. A surface of the membrane material on an outer side of the container is in contact with gas (air).

It is preferable that the inside of the container in which microorganisms or cells are being cultured is isolated from the outside in order to prevent contamination. In order to optimize the concentration of a culture medium and an amount of a liquid in the culture container, the culture system according to the present invention preferably includes a sensor (not shown) that detects an amount of the liquid in the container, and the liquid supply device 240 capable of supplying the liquid into the container and adjusting the amount of the liquid in the container. The sensor that detects the amount of the liquid may be, for example, a float-type liquid level displacement sensor disposed in the container, or a sensor that optically detects a liquid level from the outside of the container. The liquid supply device 240 used in conjunction with the sensor can replenish the culture medium into the container and adjust a component concentration of the concentrated culture medium by the evaporation of water when the sensor detects that the amount of the liquid is changed by, for example, evaporation of water in the culture medium. It is possible to adjust the components of the culture medium in the container by adding or removing the components of the culture medium to be supplied as necessary.

Figure 3:
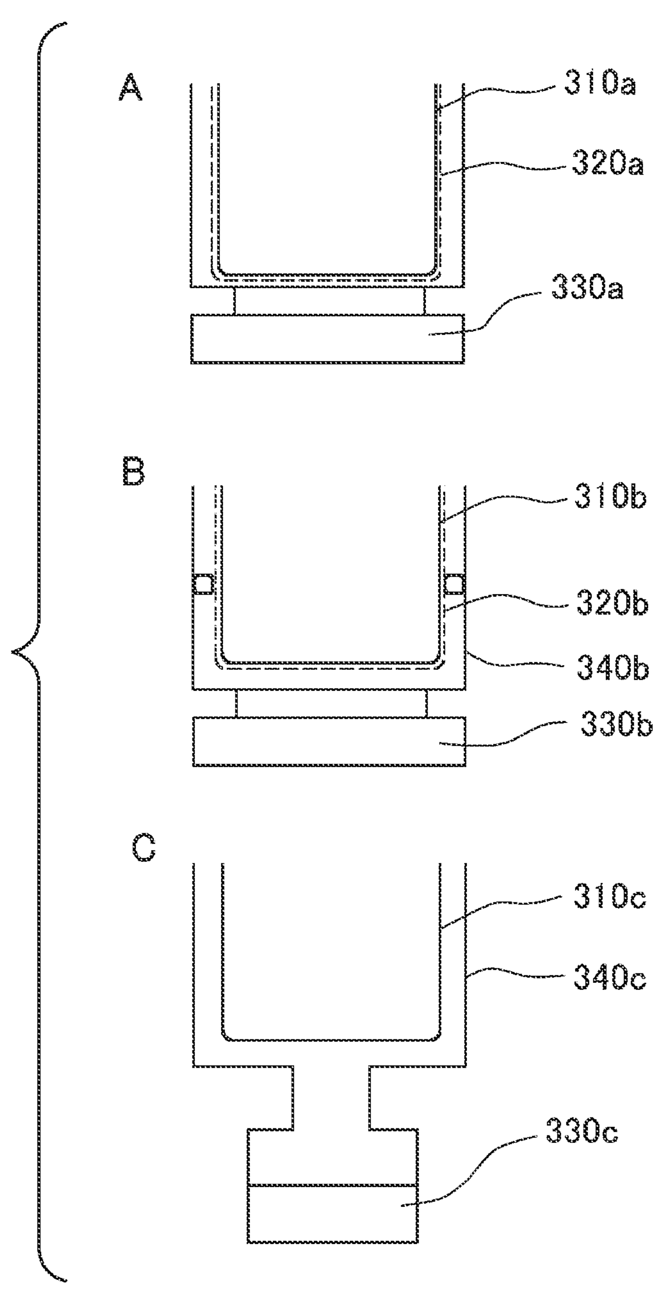
FIG. 3 is a diagram illustrating an example of a temperature adjusting device of a culture system according to the present invention.

A to C of FIG. 3 are diagrams showing an example of a temperature adjusting device that adjusts a temperature of the liquid in the gas-permeable container in the culture system according to the present invention. In the culture of microorganisms or cells, it is often necessary to keep the culture medium at a constant temperature, and the culture system according to the present invention preferably includes the temperature adjusting device that adjusts the temperature of the liquid in the gas-permeable container. An example of a method for raising the temperature of the liquid in the gas-permeable container will be described with reference to FIG. 3. In A of FIG. 3, a gas-permeable container **310*a* is disposed in a metal mesh holder 320*a*, a liquid in the gas-permeable container 310*a* is warmed through the holder 320*a* heated by a heater (such as a hot plate) 330*a* disposed under the gas-permeable container 310*a*. In B of FIG. 3, a gas-permeable container 310*b* is disposed inside a holder 320*b*, and a constant temperature chamber 340*b* is disposed outside the holder 320*b* with a gap from the holder 320*b*. A space between the holder 320*b* and 340*b* is filled with a medium such as air, a medium in the constant temperature chamber 340*b* is warmed by a heater (such as a hot plate) 330*b* disposed below the constant temperature chamber 340*b*, thereby warming the liquid in the gas-permeable container 310*b*. In C of FIG. 3, a gas-permeable container 310*c* is disposed in a tank 340*c* with an open upper portion, the tank 340*c* is warmed by blowing air for adjusting the temperature from a hot air blower 330*c*, and the liquid in the gas-permeable container 310*c* in the tank 340*c*** is warmed.

Figure 4:
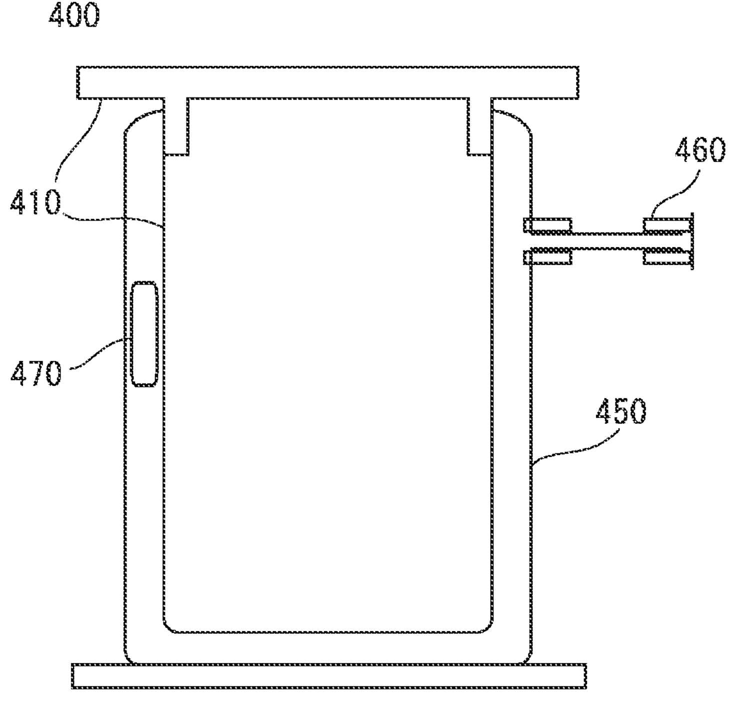
FIG. 4 is a diagram showing an example of an embodiment of the culture system according to the present invention.

FIG. 4 shows an example of an embodiment of a culture system using a culture apparatus including the gas-permeable container according to the present invention. FIG. 4 is a diagram showing the periphery of the gas-permeable container in the culture system, and a culture system 400 includes a gas-permeable container 410 and an outer wall 450 covering the periphery of the gas-permeable container 410. The gas-permeable container 410 stores a liquid inside during use, and a surface, on an inner side of the gas-permeable container, of a membrane material constituting the gas-permeable container 410 is in contact with the liquid.

A surface, on an outer side of the container, of the membrane material of the gas-permeable container is in contact with gas (air).

The outer wall 450 is preferably made of a material having a certain degree of barrier properties, such as resin or metal with solid structure. Further, a part of the outer wall 450 may be open, and a joint 460 provided with a sterile filter or the like may be connected to the opening as a gas communication unit. It is preferable that a space between the gas-permeable container 410 and the outer wall 450 is a structure that can secure a constant gap by using a spacer 470 or the like. Gas can be sent into the space between the gas-permeable container 410 and the outer wall 450 through the joint 460 provided with the sterile filter or the like. For example, an environment inside the gas-permeable container can be adjusted to be constant by sending gas whose temperature and humidity are adjusted, or by sending gas in which a concentration of gas components such as oxygen is adjusted.

Figure 5:
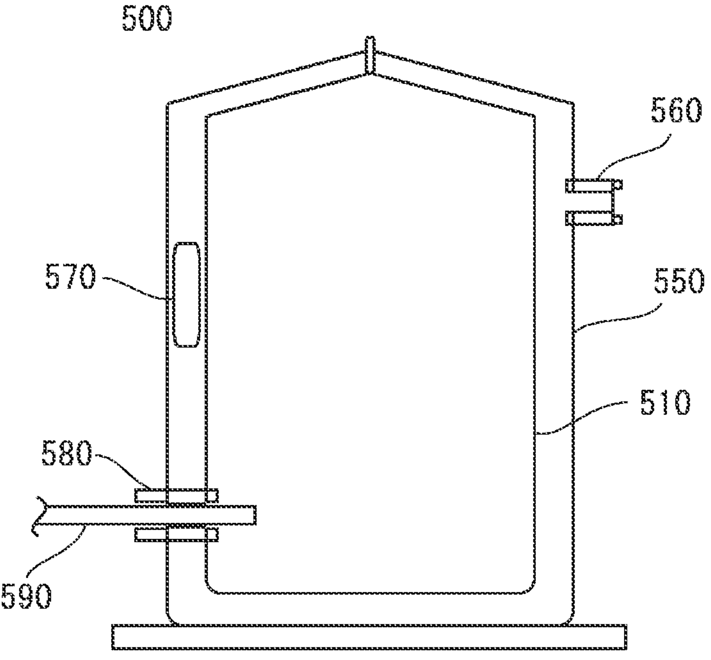
FIG. 5 is a diagram showing an example of an embodiment of the culture system according to the present invention.

Further, FIG. 5 shows another example of an embodiment of the culture system using the culture apparatus including the gas-permeable container according to the present invention. A culture system 500 includes a gas-permeable container 510 and an outer wall 550 covering the periphery of the gas-permeable container 510. Similar to the example of FIG. 4, the gas-permeable container 510 stores a liquid inside during use, and a surface, on an inner side of the gas-permeable container, of a membrane material constituting the gas-permeable container 510 is in contact with the liquid. A surface, on an outer side of the container, of the membrane material of the gas-permeable container is in contact with gas (air). The outer wall 550 is preferably made of a material having a certain degree of barrier properties, such as resin or metal with solid structure. Further, a part of the outer wall 550 may be open, and a joint 560 provided with a sterile filter or the like may be connected to the opening as a gas communication unit. It is preferable that a space between the gas-permeable container 510 and the outer wall 550 is a structure that can secure a constant gap by using a spacer 570 or the like. Gas can be sent into the space between the gas-permeable container 510 and the outer wall 550 through the joint 560 provided with the sterile filter or the like. For example, an environment inside the gas-permeable container can be adjusted to be constant by sending gas whose temperature and humidity are adjusted, or by sending gas in which a concentration of gas components such as oxygen is adjusted.

Further, in the culture system 500, sensors 590 such as a temperature sensor, a sensor that detects an amount of the liquid, an oxygen concentration sensor, and a pH sensor are provided via a special joint 580 attached to the gas-permeable container 510, and the culture medium and necessary components can be supplied through the special joint 580.

Figure 6:
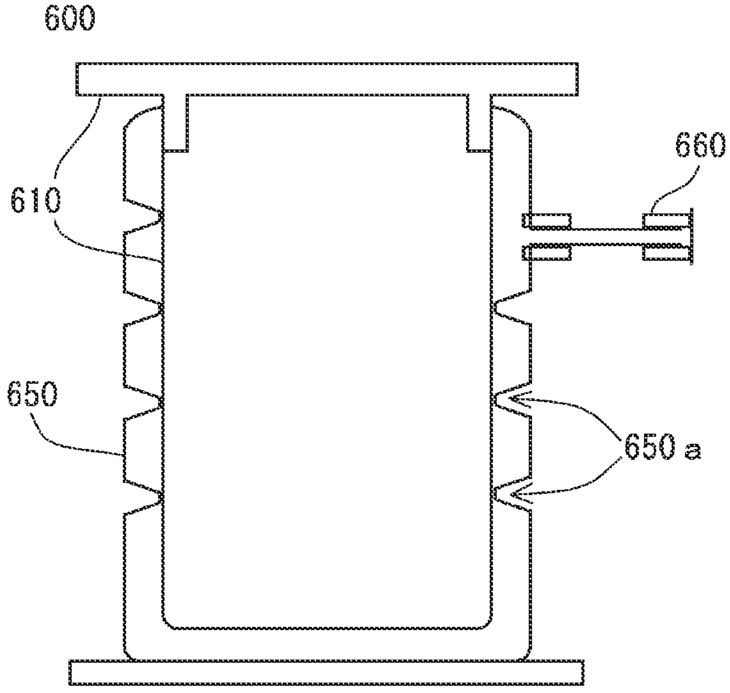
FIG. 6 is a diagram showing an example of an embodiment of the culture system according to the present invention.

FIG. 6 shows another example of an aspect of the outer wall covering the periphery of the container of the culture system, taking the culture system shown in FIG. 4 above as an example. In the example of FIG. 6, a culture system 600 includes a gas-permeable container 610 and an outer wall 650 covering the periphery of the gas-permeable container 610. The outer wall 650 is preferably made of a material having a certain degree of barrier properties, such as resin or metal with solid structure. Further, a structure in which an opening is provided in a part of the outer wall 650 and a joint 660 provided with a sterile filter or the like is connected as a gas communication unit may be used. The outer wall 650 has one or more projections **650*a* directed toward the gas-permeable container 610, and the projection 650*a* can ensure a constant gap between the gas-permeable container 610 and the outer wall 650. Gas can be sent into a space between the gas-permeable container 610 and the outer wall 650 through the joint 660** provided with the sterile filter or the like. For example, an environment inside the gas-permeable container can be adjusted to be constant by sending gas whose temperature and humidity are adjusted, or by sending gas in which a concentration of gas components such as oxygen is adjusted.

Figure 7:
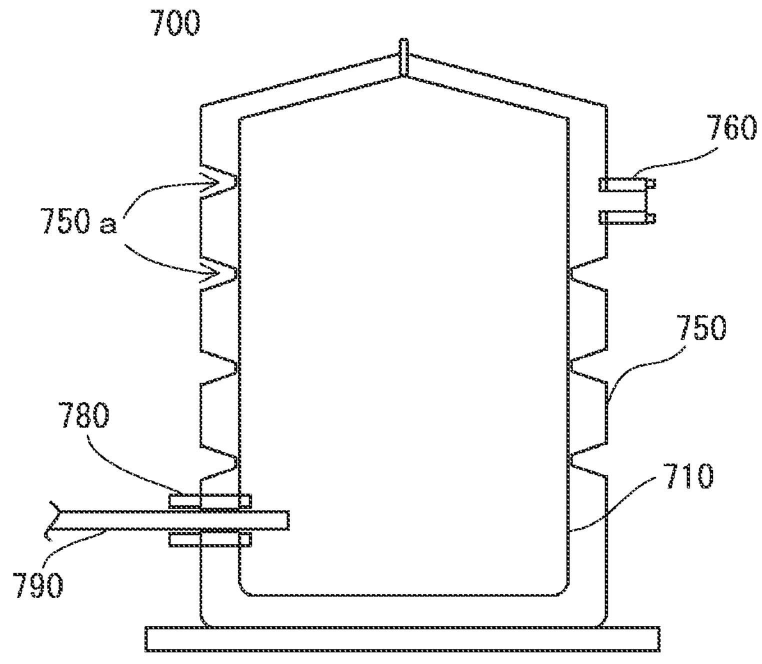
FIG. 7 is a diagram showing an example of an embodiment of the culture system according to the present invention.

Further, FIG. 7 shows another example of an aspect of the outer wall covering the periphery of the container of the culture system, taking the culture system shown in FIG. 5 above as an example. In the example of FIG. 7, a culture system 700 includes a gas-permeable container 710 and an outer wall 750 covering the periphery of the gas-permeable container 710. The outer wall 750 is preferably made of a material having a certain degree of barrier properties, such as resin or metal with solid structure. Further, a structure in which an opening is provided in a part of the outer wall 750 and a joint 760 provided with a sterile filter or the like is connected as a gas communication unit may be used. The outer wall 750 has one or more projections **750*a* directed toward the gas-permeable container 710, and the projection 750*a* can ensure a constant gap between the gas-permeable container 710 and the outer wall 750. Gas can be sent into a space between the gas-permeable container 710 and the outer wall 750 through the joint 760** provided with a sterile filter or the like. For example, an environment inside the gas-permeable container can be adjusted to be constant by sending gas whose temperature and humidity are adjusted, or by sending gas in which a concentration of gas components such as oxygen is adjusted.

Further, in the culture system 700, sensors 790 such as a temperature sensor, a sensor that detects an amount of liquid, an oxygen concentration sensor, and a pH sensor are provided via a special joint 780 attached to the gas-permeable container 710, and the culture medium and necessary components can be supplied through the special joint 780.

Generally, in fed-batch culture, a culture medium containing nutrients is added to a culture container during a culture process, and an adding amount is limited due to an increase in an amount of the culture medium in the culture container. In the culture system using the gas-permeable container according to the present invention, unnecessary moisture and gas components in the gas-permeable container can be easily discharged out of the gas-permeable container, and thus, for example, an amount of the liquid in the gas-permeable container and a concentration of the nutrients can be adjusted within certain ranges from the start to the end of the culture, and the fed-batch culture can be performed while the unnecessary gas components are discharged. Further, the fed-batch culture can be performed more effectively by using, in combination, a liquid supply device capable of detecting an amount of the liquid in the gas-permeable container with a sensor, supplying the liquid into the gas-permeable container, and adjusting the amount of the liquid in the gas-permeable container. Further, the gas-permeable container according to the present invention can also be suitably used for perfusion culture in which a culture medium in a culture container is filtered and discharged, and the culture medium and necessary components are supplied and cultured while adjusting the amount of a liquid in the culture container.

The gas-permeable container according to the present invention is described in more detail in Examples below.

The following Examples are intended to illustrate the invention, and the content of the present invention is not limited by the following Examples.

EXAMPLES

<Calculation of Ratio of Water Evaporation Amounts>

The ratio of water evaporation amounts of the present invention is defined by the following formula.

Ratio of water evaporation amounts=WE (WET)/WE (DRY)

WE (DRY) (kg/($m^2$·h): water evaporation amount in a state where the membrane material is not in contact with water WE (WET) (kg/($m^2$·h): water evaporation amount in a state where the membrane material is in contact with water The above water evaporation amounts are water evaporation amounts inside a moisture-permeable cup through the membrane material in a state where water is poured into the moisture-permeable cup and a window of the moisture-permeable cup is sealed with the membrane material, and the measurement is performed in accordance with an ASTM E96B method. WE (DRY) is measured by placing in a constant temperature and humidity chamber in a state where the window of the moisture-permeable cup closed with the membrane material faces upward, and WE (WET) is measured by placing in the constant temperature and humidity chamber in a state where the window of the moisture-permeable cup closed with the membrane material faces downward.

Specifically, the measurement was performed as follows. A circular piece with a diameter of 70 mm was cut out from the membrane material of the gas-permeable container to be measured. When the gas-permeable container has a complicated structure, the water evaporation amount is measured at a portion of the gas-permeable container which has highest oxygen permeability.

The moisture-permeable cup was filled with 30 g of water, the window (diameter 60 mm) of the moisture-permeable cup was closed with the cut out part of the membrane material, the moisture-permeable cup was placed in a constant temperature and humidity chamber stabilized at a temperature of 37° C. and a humidity of 50% RH, and was taken out at regular time intervals to measure weight loss of water. The above water evaporation amount kg/($m^2$·h) was calculated based on a time until a weight of water in the moisture-permeable cup decreases by 10% from the weight before the test, an amount of weight loss of water at that time, and an area of the window of the moisture-permeable cup (an area where the membrane material is exposed to the outside of the moisture-permeable cup). Until the measurement was completed, the membrane material covering the window of the moisture-permeable cup was kept in a state where foreign matter is not brought into contact.

In the above-described measurement of the ratio of the water evaporation amounts, if WE (WET) of about 0.01 kg/($m^2$·h) or more, it is easy to accurately calculate the ratio of water evaporation amounts. In this regard, WE (WET) is preferably about 0.02 kg/($m^2$·h) or more, further preferably about 0.05 kg/($m^2$·h) or more, and most preferably about 0.1 kg/($m^2$·h) or more. In order to accurately calculate the ratio of water evaporation amounts by the above measurement, measurement conditions may be devised such that a period of measurement does not exceed, for example, three days.

<Measurement of Volumetric Oxygen Transfer Coefficient $k_La$>

1 L of pure water is poured into a gas-permeable container with a capacity of 3 L provided with a stirring blade and an electrode dissolved oxygen meter, and the pure water in the container is stirred by rotating the stirring blade at a rotation speed of 80 rpm. The pure water in the container described above is sufficiently bubbled with nitrogen gas to bring a dissolved oxygen concentration of the water close to 0 mg/L. After the dissolved oxygen concentration stabilizes, the bubbling is stopped and the dissolved oxygen concentration is continuously measured until the dissolved oxygen concentration of water is saturated. A volumetric oxygen transfer coefficient $k_La$ ($h^{-1}$) is calculated from a relationship between the dissolved oxygen concentration and the time.

<Water Pressure Resistance Test>

The container is sealed such that water does not flow in or out except through a water injection port for injecting water into the container, and water is injected into the container. A water pressure at which water is injected into the container before the water injection port is measured, and the water pressure at which water seeps out of the container is observed. If measurement cannot be performed in a container because the container is large, the membrane material at a place where the water pressure resistance is assumed to be the lowest in the container (in the case of the container according to the present invention, the place is often a part of the gas-permeable membrane material) and the measurement is performed according to the following procedure.

Figure 8:
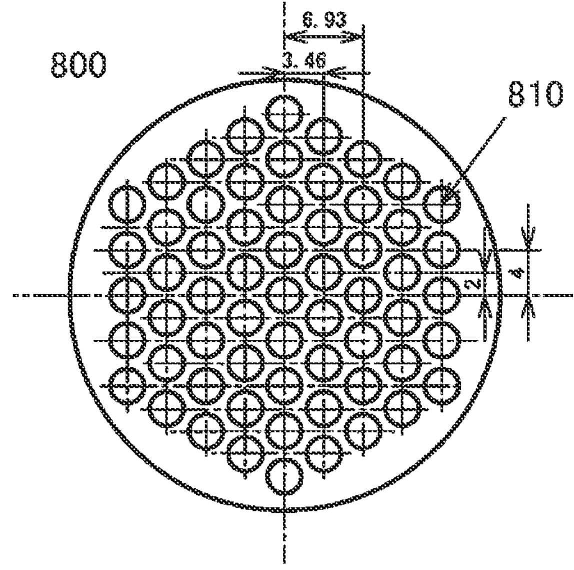
FIG. 8 is a diagram of a support plate that supports a membrane material when measuring a water pressure resistance.
Figure 9:
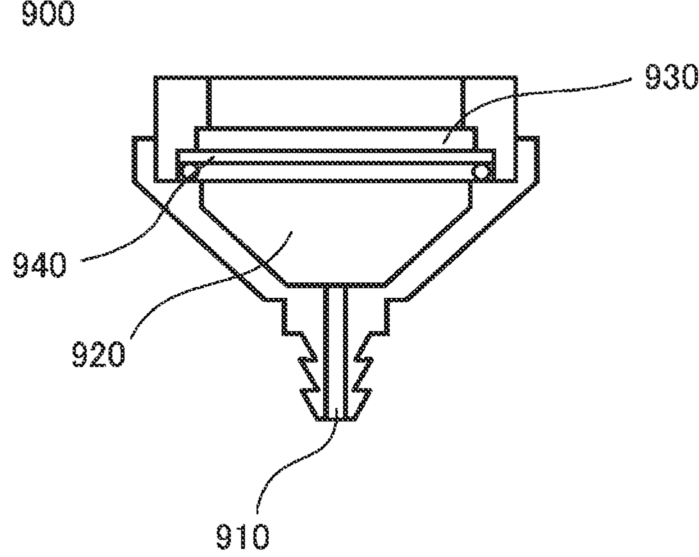
FIG. 9 is a schematic diagram of a measurement holder that measures the water pressure resistance.

A part of the membrane material of the gas-permeable container to be measured is cut into a circular shape with a diameter of 50 mm, and is overlapped with the support plate. The support plate uses one having a strength strong enough not to be deformed by pressure. In the present measurement, a circular stainless steel plate having a thickness of 2 mm and a diameter of 38 mm was used as a support plate 800, in which 61 holes 810 having a diameter of 3 mm were evenly arranged from the center (see FIG. 8). A part of the cut membrane material overlaps the support plate, and is disposed in a measurement holder 900 shown in FIG. 9 in a manner that the support plate faces upward. Water is injected into a pressurization chamber 920 from a water injection port 910 and pressurized. When the pressure is gradually increased, the water passes through a membrane material 940 supported by the support plate 930, and when water is confirmed as water droplets or spouted out at two or more places on an upper surface of the membrane material 940, the pressure is read and regarded as a water pressure resistance of the membrane material, and is adopted as water pressure resistance of the gas-permeable container with the membrane material as a part.

<Measurement of Water Evaporation Amount Per Unit Liquid Contact Area of Container>

The water evaporation amount per unit liquid contact area of the container is measured based on a normal usage of a gas-permeable container to be measured. Specifically, the measurement is as follows.

1) Pour Water in Container

Pure water is poured up to near an upper limit of the normal usage of the gas-permeable container to be measured.

2) Dispose Container in Special Environment

The closed gas-permeable container is disposed in an environment with a temperature of 37° C. and a humidity of 50% RH in the normal usage for that container.

3) Observation of Change Over Time

Regarding the weight of water in the container, change over time is observed until water decreases by 10% from water before the test, and an amount of water evaporated from the sealed container per hour is calculated based on the amount of water evaporated from the container up to a time point of 10% reduction.

4) Calculate Water Evaporation Amount Per Unit Liquid Contact Area of Container

The water evaporation amount per unit liquid contact area (kg/($m^2$·h)) of the container is calculated using the following formula.

(water evaporation amount per unit liquid contact area of container)=(amount of water evaporated from sealed container per hour)/(area of inner surface of container in contact with the water when water is poured into container)

<Bubble Point Measurement>

When the sheet with porous structure is used as the membrane material of the gas-permeable container, a bubble point is measured. The measurement is performed in accordance with JIS K3832. A circular piece with a diameter of 50 mm was cut out from the membrane material of the gas-permeable container. When the gas-permeable container is made of a plurality of membrane materials with different structures, the bubble point is measured at a portion with a smallest bubble point in the material forming the gas-permeable container.

Figure 10:
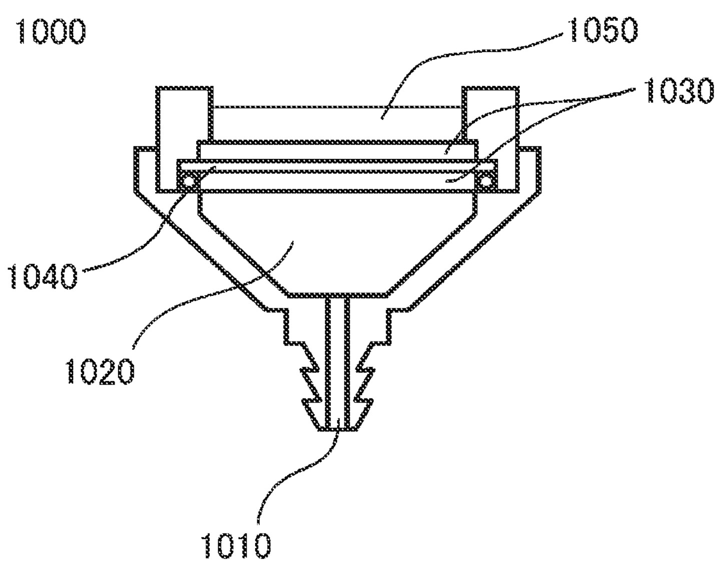
FIG. 10 is a schematic diagram of a measurement holder that measures a bubble point.

A part of the cut membrane material is sandwiched between two support plates. The support plate uses the one same as the support plate used in the measurement of water pressure resistance. The membrane material sandwiched between the support plates is disposed in a measurement holder 1000 shown in FIG. 10. An isopropyl alcohol (IPA) layer 1050 is formed on support plates 1030 and a membrane material 1040, and nitrogen gas is injected into a pressurization chamber 1020 from an injection port 1010 to be pressurized. When the pressure is gradually increased, nitrogen gas passes through the membrane material 1040 and appears as continuous bubbles in the IPA layer 1050 on an upper surface of the membrane material, a pressure is read and taken as a bubble point bp of the membrane material.

A bubble point change rate Δbp between a bubble point bp1 before the water pressure resistance test and a bubble point bp2 after the water pressure resistance test of the sheet with porous structure is obtained by the following Formula (1).

$$\Delta bp=(|bp1-bp2|)/bp1 \quad \text{Formula (1)}$$

Example 1

A sheet with porous structure of PTFE was prepared. An aluminum mandrel having a diameter of 100 mm and a length of 500 mm was used, and the prepared sheet with porous structure of PTFE was wound 20 times on the mandrel to form a cylindrical laminate. A circular sheet with porous structure of PTFE serving as a bottom of a container was attached to one end of the obtained laminate of the sheet with porous structure of PTFE, and thereby a beaker-shaped laminate was formed. The formed beaker-shaped laminate of the sheet with porous structure of PTFE was sintered by being heated in an oven at a temperature of 360° C. or higher for 60 minutes while covering the mandrel. The sintered beaker-shaped PTFE laminate was cooled in the oven until residual heat was removed, and after being removed from the mandrel, was attached with a fluororesin lid, and thereby the gas-permeable container according to the present invention was obtained. In the obtained gas-permeable container, a thickness of a sidewall thereof was about 0.31 mm and a capacity thereof was about 3.5 L. Regarding the obtained gas-permeable container, a sample of the membrane material was cut from the sidewall of the gas-permeable container, and the ratio of water evaporation amounts was calculated according to the method described above and was 2.1.

Example 2

A sheet with porous structure of PTFE different from Example 1 was prepared. Similar to Example 1, the sheet with porous structure of PTFE was wound on a mandrel to have a thickness of about 0.08 mm, a circular sheet with porous structure of PTFE was attached, and a beaker-shaped laminate was formed. The formed beaker-shaped laminate of the sheet with porous structure of PTFE was sintered by being heated in an oven at a temperature of 370° C. or higher for 40 minutes while covering the mandrel. The sintered beaker-shaped PTFE laminate was cooled in the oven until residual heat was removed, and after being removed from the mandrel, was attached with a fluororesin lid, and thereby the gas-permeable container according to the present invention was obtained. Regarding the obtained gas-permeable container, a sample of the membrane material was cut from a sidewall of the gas-permeable container, and the ratio of water evaporation amounts was calculated according to the method described above and was 2.8.

Example 3

A sheet with porous structure of PTFE different from Example 1 was prepared. Similar to Example 1, the sheet with porous structure of PTFE was wound on a mandrel to have a thickness of about 3.0 mm, a circular sheet with porous structure of PTFE was attached, heated, and removed from the mandrel, and then a fluororesin lid was attached, and the gas-permeable container according to the present invention was obtained. Regarding the obtained gas-permeable container, a sample of the membrane material was cut from a sidewall of the gas-permeable container, and the ratio of water evaporation amounts was calculated according to the method described above and was 1.3.

Example 4

A high-density polyethylene nonwoven fabric (Tyvek 1073B manufactured by DuPont) was prepared. Similar to Example 1, the high-density polyethylene nonwoven fabric was wound on a mandrel, a circular sheet was attached, heated, and removed from the mandrel, and then a fluororesin lid was attached, and the gas-permeable container according to the present invention was obtained. Regarding the obtained gas-permeable container, a sample of the membrane material was cut from a sidewall of the gas-permeable container, and the ratio of water evaporation amounts was calculated according to the method described above and was 1.4.

Example 5

A rectangular sheet with solid structure of PFA and a long side of about 360 mm and a short side of about 240 mm and a sheet with porous structure of PTFE were prepared. Further, an aluminum mandrel having a diameter of 120 mm and a length of 270 mm was prepared. The prepared sheet with porous structure of PTFE was wound five times on the mandrel, and then the prepared sheet with solid structure of PFA was overlapped thereon in a manner that the short side of the sheet was parallel to an axial direction of the mandrel, and further wound five times, and thereby a cylindrical laminate was formed. A circular sheet with porous structure of PTFE serving as a bottom of a container was attached to one end of the obtained cylindrical laminate, and a beaker-shaped laminate was formed. The formed beaker-shaped laminate was sintered by being heated in an oven at a temperature of 360° C. or higher for 60 minutes while covering the mandrel. The sintered beaker-shaped laminate was cooled in the oven until residual heat was removed, removed from the mandrel, and attached with a fluororesin lid, and the gas-permeable container according to the present invention was obtained. Regarding the obtained gas-permeable container, the water evaporation amount per unit liquid contact area of the container was measured according to the method described above and was 0.09 kg/(m$^2$·h).

Example 6

A sheet with porous structure of PTFE different from Example 1 was prepared. The same mandrel as in Example 5 was used, a sheet with porous structure of PTFE was wound 10 times on the mandrel, heated, and removed from the mandrel, and then cut open into a square to obtain one laminate. A joint serving as a water injection port was attached to the laminate and folded in half. Four sides of the folded laminate were fused with a heat sealer so as to form a closed shape, and the gas-permeable container according to the present invention was obtained. Regarding the obtained gas-permeable container, the water evaporation amount per unit liquid contact area of the container was measured according to the method described above and was 0.19 kg/(m$^2$·h).

Example 7

A rectangular sheet with solid structure of PFA and a long side of about 380 mm and a short side of about 240 mm and a sheet with porous structure of PTFE having were prepared. Similar to Example 5, the prepared sheet with porous structure of PTFE was wound five times on the mandrel, and then the prepared sheet with solid structure of PFA was overlapped thereon in a manner that the short side of the sheet was parallel to an axial direction of the mandrel, and further wound five times, and thereby a cylindrical laminate was formed. A circular sheet which was served as a bottom of the container and was made by laminating the sheet with porous structure of PTFE and the sheet with solid structure of PFA was attached to one end of the cylindrical laminate, and a beaker-shaped laminate was formed. The formed beaker-shaped laminate was sintered by being heated in an oven at a temperature of 360° C. or higher for 60 minutes while covering the mandrel. The sintered beaker-shaped laminate was cooled in the oven until residual heat was removed, removed from the mandrel, and attached with a fluororesin lid, and the gas-permeable container according to the present invention was obtained. Regarding the obtained gas-permeable container, the water evaporation amount per unit liquid contact area of the container was measured according to the method described above and was 0.05 kg/(m$^2$·h).

Comparative Example

A container having a sidewall made of silicone rubber and a thickness of mm was prepared. A sample of the membrane material was cut out from the prepared container made of silicone rubber, and the water evaporation amount was measured according to the method described above, and WE (WET) was kg/(m$^2$·h).

Regarding the containers of Examples 1 and 2, results of measuring the water evaporation amount per unit liquid contact area of the container, the water pressure resistance, and the bubble point before and after the water pressure resistance test were shown in Table 1. It can be seen that the gas-permeable containers of Examples 1 and 2 are excellent not only in water evaporation efficiency but also in strength and durability of a container.

TABLE 1

| | Ratio of water evaporation amounts | Water evaporation amount per unit liquid contact area of container (kg/(m2 · h)) | Water pressure resistance (kPa) | Bubble point before water pressure resistance test (kPa) | Bubble point change rate Δbp (%) |
|---|---|---|---|---|---|
| Example 1 | 2.1 | 0.20 | 559 | 153 | 6.7 |
| Example 2 | 2.8 | 0.29 | 367 | 126 | 3.9 |
| Example 3 | 1.3 | — | — | — | — |
| Example 4 | 1.4 | — | — | — | — |
| Example 5 | 2.4 | 0.09 | — | — | — |
| Example 6 | 2.4 | 0.19 | — | — | — |
| Example 7 | 2.4 | 0.05 | — | — | — |

The gas-permeable container, and the culture apparatus and culture system each using the container according to the present invention have been described above, but the present invention is not limited thereto, and can be modified as appropriate without departing from the gist of the invention.

INDUSTRIAL APPLICABILITY

A gas-permeable container according to the present invention has excellent gas permeability. For example, if the gas-permeable container according to the present invention is used, it is possible to maintain a high dissolved oxygen concentration of a liquid in the container, and at the same time, it is possible to moderately discharge gaseous waste products such as carbon dioxide in a culture medium, and thus, a culture system can be configured with a simple structure. Furthermore, by using the gas-permeable container according to the present invention in conjunction with various oxygen supply methods such as bubbling, higher effects in culturing aerobic microorganisms or animal or plant cells can be obtained. By using both a sensor that detects an amount of the liquid in the container and a liquid supply device capable of adjusting the amount of the liquid, culture can be performed while the amount of the liquid is adjusted in the culture medium.

REFERENCE SIGNS LIST

100 apparatus
200 culture system
210 gas-permeable container
220 holder
240 liquid supply device
400, 500, 600, 700 culture system

The invention claimed is:

1. A culture container configured to hold a liquid therein, comprising:

a membrane material, wherein the membrane material has an inner surface configured to be in contact with the liquid, and an outer surface that is opposite to the inner surface and is configured to be in contact with a gas, the membrane material is gas-permeable such that the gas is transferable into the liquid, the membrane material is a laminate comprising a plurality of porous membranes laminated together or a laminate comprising a plurality of nonwoven fabrics laminated together, wherein the membrane material forms a side and a bottom of the culture container, and wherein a water evaporation amount per unit liquid contact area of the culture container is 0.01 kg/($m^2$·h) to 1.0 kg/($m^2$·h).

2. A culture container configured to hold a liquid therein, comprising:

a membrane material, wherein the membrane material has an inner surface configured to be in contact with the liquid, and an outer surface that is opposite to the inner surface and is configured to be in contact with a gas, the membrane material is gas-permeable such that the gas is transferable into the liquid, the membrane material is a laminate comprising a plurality of porous membranes laminated together or a laminate comprising a plurality of nonwoven fabrics laminated together, wherein the membrane material forms a side and a bottom of the culture container, and wherein the membrane material has a ratio of water evaporation amounts of 1.1 or more.

3. The culture container according to claim 2, wherein the membrane material comprises at least one selected from polyolefin and fluororesin.

4. The culture container according to claim 2, wherein the culture container has a water pressure resistance of 300 kPa or more.

5. A culture container configured to hold a liquid therein, comprising:

a membrane material, wherein the membrane material has an inner surface configured to be in contact with the liquid, and an outer surface that is opposite to the inner surface and is configured to be in contact with a gas, the membrane material is gas-permeable such that the gas is transferable into the liquid, the membrane material is a laminate comprising a plurality of porous membranes laminated together or a laminate comprising a plurality of nonwoven fabrics laminated together, wherein the membrane material forms a side and a bottom of the culture container, and wherein a bubble point change rate is within 15%, the bubble point change rate being determined based on (i) a bubble point of the membrane material of the culture container before a water pressure resistance test is performed and (ii) a bubble point of the membrane material of the culture container after the water pressure resistance test is performed.

6. A culture container configured to hold a liquid therein, comprising:

a membrane material, wherein the membrane material has an inner surface configured to be in contact with the liquid, and an outer surface that is opposite to the inner surface and is configured to be in contact with a gas, the membrane material is gas-permeable such that the gas is transferable into the liquid, the membrane material is a laminate comprising a plurality of porous membranes laminated together or a laminate comprising a plurality of nonwoven fabrics laminated together, wherein the membrane material forms a side and a bottom of the culture container, and wherein the membrane material has a ratio of water evaporation amounts of 5.0 or less.

* * * * *